US008165686B2

(12) United States Patent
Zierhofer (10) Patent No.: US 8,165,686 B2
(45) Date of Patent: Apr. 24, 2012

(54) SIMULTANEOUS INTRACOCHLEAR STIMULATION

(75) Inventor: Clemens Zierhofer, Kundl (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 895 days.

(21) Appl. No.: 12/208,793

(22) Filed: Sep. 11, 2008

(65) Prior Publication Data

US 2009/0036962 A1    Feb. 5, 2009

Related U.S. Application Data

(63) Continuation-in-part of application No. 11/685,887, filed on Mar. 14, 2007, now Pat. No. 7,937,157, which is a continuation of application No. 10/303,568, filed on Nov. 25, 2002, now Pat. No. 7,209,789, which is a continuation of application No. 09/648,687, filed on Aug. 25, 2000, now Pat. No. 6,594,525.

(60) Provisional application No. 60/150,773, filed on Aug. 26, 1999, provisional application No. 60/971,473, filed on Sep. 11, 2007.

(51) Int. Cl.
*A61N 1/36* (2006.01)
(52) U.S. Cl. ........................................................ 607/57
(58) Field of Classification Search .............. 607/55–57, 607/137; 623/10
See application file for complete search history.

(56) References Cited

U.S. PATENT DOCUMENTS

| | | | |
|---|---|---|---|
| 4,284,856 A | 8/1981 | Hochmair et al. | 179/107 E |
| 4,428,377 A | 1/1984 | Zollner et al. | 128/419 R |
| 4,515,158 A | 5/1985 | Patrick et al. | 128/419 R |
| 5,215,085 A | 6/1993 | von Wallenberg-Pachaly | 128/420.6 |
| 5,549,658 A | 8/1996 | Shannon et al. | 607/57 |
| 5,601,617 A | 2/1997 | Loeb et al. | 607/56 |
| 5,609,616 A | 3/1997 | Schulman et al. | 607/56 |
| 5,749,912 A | 5/1998 | Zhang et al. | 607/57 |
| 5,824,022 A | 10/1998 | Zilberman et al. | 607/57 |

(Continued)

FOREIGN PATENT DOCUMENTS

EP    1854504    11/2007

(Continued)

OTHER PUBLICATIONS

Frijns et al., "A Model of Myelinated Nerve Fibres for Electrical Prosthesis Design", Med. & Biol. Eng. & Comput., vol. 32 No. 3, pp. 391-398, May 1994.

(Continued)

*Primary Examiner* — Carl H Layno
*Assistant Examiner* — Frances Oropeza
(74) *Attorney, Agent, or Firm* — Sunstein Kann Murphy & Timbers LLP (57) ABSTRACT

A method, system and computer product for simultaneously activating at least two electrodes in a multichannel electrode array is presented. The method includes calculating pulse amplitudes of the electrodes in the multichannel array by taking into account parameters of spatial channel interaction reflecting geometric overlapping of electrical fields from each electrode. Calculating is based, at least in part, on place-independent impulse responses characterized by a first exponential decay constant $\alpha$ at a first side of the electrode and a second exponential decay constant $\beta$ at a second side of the electrode, such that the first exponential decay constant $\alpha$ is the same for each electrode in the array, and the second exponential decay constant $\beta$ is the same for each electrode in the array.

23 Claims, 5 Drawing Sheets

U.S. PATENT DOCUMENTS

| | | | | |
|---|---|---|---|---|
| 5,938,691 | A | 8/1999 | Schulman et al. | 607/57 |
| 5,957,958 | A | 9/1999 | Schulman et al. | 607/56 |
| 6,002,966 | A | 12/1999 | Loeb et al. | 607/57 |
| 6,175,767 | B1 | 1/2001 | Doyle, Sr. | 607/57 |
| 6,219,580 | B1 | 4/2001 | Faltys et al. | 607/57 |
| 6,289,247 | B1 | 9/2001 | Faltys et al. | 607/57 |
| 6,295,472 | B1 | 9/2001 | Rubinstein et al. | 607/55 |
| 6,594,525 | B1 | 7/2003 | Zierhofer | 607/57 |
| 6,600,955 | B1 | 7/2003 | Zierhofer | 607/57 |
| 7,110,821 | B1 | 9/2006 | Ross | 607/57 |
| 7,209,789 | B2 | 4/2007 | Zierhofer | 607/57 |
| 7,937,157 | B2 | 5/2011 | Zierhofer | 607/57 |
| 2001/0031909 | A1 | 10/2001 | Faltys et al. | 600/25 |
| 2004/0082985 | A1 | 4/2004 | Faltys et al. | 607/116 |
| 2005/0203590 | A1 | 9/2005 | Zierhofer | 607/57 |
| 2006/0195160 | A1* | 8/2006 | Blamey et al. | 607/57 |
| 2007/0156202 | A1 | 7/2007 | Zierhofer | 607/57 |

FOREIGN PATENT DOCUMENTS

| | | |
|---|---|---|
| EP | 228507 | 7/2010 |
| WO | WO 98/49775 | 11/1998 |
| WO | WO 99/35882 | 7/1999 |
| WO | WO 99/49815 | 10/1999 |
| WO | WO 01/13991 | 3/2001 |
| WO | WO 01/19304 | 3/2001 |
| WO | WO 2005/113064 | 12/2005 |
| WO | WO 2006/136961 | 12/2006 |

OTHER PUBLICATIONS

Liang et al., "A Method for Evaluating the Selectivity of Electrodes Implanted for Nerve Simulation" IEEE Transactions on Biomedical Engineering, vol. 38 No. 5, pp. 443-449, May 1991.

Smith et al., "Chimaeric Sounds Reveal Dichotomies in Auditory Perception", NIH-PA Author Manuscript, PMC 2008, Mar. 17, pp. 1-10.

Zeng et al., "Speech Recognition with Amplitude and Frequency Modulations", PNAS, vol. 102, No. 7, pp. 2293-2298, Feb. 2005.

European Patent Office, European Search Report—European Application No. EP 10003323.2-2305, dated Jun. 22, 2010, 6 pages.

European Patent Office, Examination Report—European Application No. 07075655.6-2305, dated Aug. 26, 2010, 4 pages.

European Patent Office, Communication Pursuant to Article 94(3) EPC—European Application No. 07075655.6-2305, dated Jun. 8, 2009, 1 page.

Clive Froud & Co Limited, Response dated Oct. 12, 2009, pertaining to European Application No. 07075655.6-2306, 6 pages.

United States Patent and Trademark Office, Office Action dated Jan. 3, 2002, pertaining to U.S. Appl. No. 09/648,687, 13 pages.

Bromberg & Sunstein LLP, response dated Apr. 2, 2002, pertainig to U.S. Appl. No. 09/648,687, 14 pages.

United States Patent and Trademark Office, Office Action dated Jun. 26, 2002, pertaining to U.S. Appl. No. 09/648,687, 7 pages.

Bromberg & Sunstein LLP, Response dated Sep. 11, 2002, pertaining to U.S. Appl. No. 09/648,687, 5 pages.

United States Patent and Trademark Office, Interview Summary dated Sep. 16, 2002, pertaining to U.S. Appl. No. 09/648,687, 10 pages.

United States Patent and Trademark Office, Advisory Action and Interview Summary dated Oct. 1, 2002, pertaining to U.S. Appl. No. 09/648,687, 6 pages.

Bromberg & Sunstein LLP, Amendment dated Nov. 25, 2002, pertaining to U.S. Appl. No. 09/648,687, 12 pages.

United States Patent and Trademark Office, Interview Summary dated Dec. 9, 2002, pertaining to U.S. Appl. No. 09/648,687, 2 pages.

United States Patent and Trademark Office, Notice of Allowance and Fee(s) Due dated Dec. 16, 2002, pertaining to U.S. Appl. No. 09/648,687, 9 pages.

Bromberg & Sunstein LLP, Election and Preliminary Amendment dated Mar. 3, 2006, pertaining to U.S. Appl. No. 10/303,568, 6 pages.

United States Patent and Trademark Office, Office Action dated Mar. 31, 2006, pertaining to U.S. Appl. No. 10/303,568, 11 pages.

Bromberg & Sunstein LLP, Response dated Sep. 28, 2006, pertaining to U.S. Appl. No. 10/303,568, 8 pages.

United States Patent and Trademark Office, Interview Summary dated Oct. 6, 2006, pertaining to U.S. Appl. No. 10/303,568, 4 pages.

United States Patent and Trademark Office, Notice of Allowance and Fee(s) Due dated Dec. 19, 2006, pertaining to U.S. Appl. No. 10/303,568, 5 pages.

United States Patent and Trademark Office, Office Action dated Jan. 31, 2008, pertaining to U.S. Appl. No. 11/101,149, 5 pages.

Bromberg & Sunstein LLP, Response dated Feb. 29, 2008, pertaining to U.S. Appl. No. 11/101,149, 7 pages.

United States Patent and Trademark Office, Office Action dated May 16, 2008, pertaining to U.S. Appl. No. 11/101,149, 10 pages.

Bromberg & Sunstein LLP, Response dated Aug. 15, 2008, pertaining to U.S. Appl. No. 11/101,149, 7 pages.

United States Patent and Trademark Office, Office Action dated Dec. 16, 2008, pertaining to U.S. Appl. No. 11/101,149, 12 pages.

Bromberg & Sunstein LLP, Response After Final Rejection dated Mar. 16, 2009, pertaining to U.S. Appl. No. 11/101,149, 8 pages.

United States Patent and Trademark Office, Advisory Action dated Apr. 1, 2009, pertaining to U.S. Appl. No. 11/101,149, 3 pages.

Bromberg & Sunstein LLP, Request for Continued Examination dated May 15, 2009, pertaining to U.S. Appl. No. 11/101,149, 12 pages.

United States Patent and Trademark Office, Office Action dated Jul. 30, 2009, pertaining to U.S. Appl. No. 11/101,149, 9 pages.

Sunstein Kann Murphy & Timbers LLP, Response dated Oct. 29, 2009, pertaining to U.S. Appl. No. 11/101,149, 13 pages.

United States Patent and Trademark Office, Office Action dated Mar. 4, 2010, pertaining to U.S. Appl. No. 11/101,149, 8 pages.

United States Patent and Trademark Office, Interview Summary dated Mar. 24, 2010, pertaining to U.S. Appl. No. 11/101,149, 4 pages.

United States Patent and Trademark Office, Interview Summary dated Jul. 30, 2010, pertaining to U.S. Appl. No. 11/101,149, 4 pages.

Sunstein Kann Murphy & Timbers LLP, Response to Restriction Requirement dated Apr. 30, 2010, pertaining to U.S. Appl. No. 11/685,887, 7 pages.

United States Patent and Trademark Office, Office Action dated Aug. 2, 2010, pertaining to U.S. Appl. No. 11/685,887, 6 pages.

Brummer et al., "Electrical Stimulation with Pt Electrodes: II—Estimation of Maximum Surface Redox (Theoretical Non-Gassing) Limits", *IEEE Trans. On Biomed Eng*, vol. BME 24, No. 5, pp. 440-443, Sep. 1977.

Greenwood, "A Cochlear Frequency-Position Function for Several Species—29 years later", *J. Acoust. Soc. Am*. vol. 87 (6), pp. 2592-2605, Jun. 1990.

Kasper et al., "Intracochlear Potential Distribution with Intracochlear and Extracochlear Electrical Stimulation in Humans", *Ann Otol Rhinol Laryngol*, vol. 100, pp. 812-816, 1991.

Loizou et al., "Comparison of Speech Processing Strategies Used in the Clarion Implant Processor", *Ear & Hearing*, vol. 24, No. 1, pp. 12-19, 2003.

Loizou et al., "The Effect of Parametric Variations of Cochlear Implant Processors on Speech Understanding", *J. Acoust. Soc. Am.*, vol. 108 (2), pp. 790-802, Aug. 2000.

McNamara et al., "Theory of Stochastic Resonance", *The American Physical Society*, vol. 39, No. 9, pp. 4854-4869, May 1989.

Mens et al., "Speech Perception with Mono- and Quatrupolar Electrode Configurations: A Crossover Study", *Otology & Neurotology*, vol. 26, No. 5, pp. 957-964, 2005.

Miyoshi et al., "Evaluation of the Tripolar Electrode Stimulation Method by numerical Analysis and Animal Experiments for Cochlear Implants", *Acta Otolaryngol (Stockh)*, Suppl. 532, pp. 123-125, 1997.

Morse et al., "Additive Noise Can Enhance Temporal Coding in a Computational Model of Analogue Cochlear Implant Simulation", *Hearing Research*, vol. 133, pp. 107-119, 1999.

Rubinstein et al., "Pseudospontaneous Activity: Stochastic Independence of Auditory Nerve Fibers with Electrical Stimulation", *Hearing Research*, vol. 127, pp. 108-118, 1999.

Smith et al., "Chimaeric Sounds Reveal Dichotomies in Auditory Perception", *Nature*, vol. 416, pp. 87-90, Mar. 2002.

Suesserman et al., "Lumped-Parameter Model for In Vivo Cochlear Stimulation", *IEEE Trans. On Biomed Eng*, vol. 40, No. 3, pp. 237-245, Mar. 1993.

Townshend et al., "Reduction of Electrical Interaction in Auditory Prostheses", *IEEE Trans. On Biomed Eng*, vol. BME 34, No. 11, pp. 891-896, Nov. 1987.

Van den Honert et al., "Single Fiber Mapping of Spatial Excitation Patterns in the Electrically Stimulated Auditory Nerve", *Hearing Research*, vol. 29, pp. 195-206, 1987.

Vanpoucke et al., "The Facial Nerve Canal: An Important Cochlear Conduction Path Revealed by Clarion Electrical Field Imaging", *Otology & Neurotology*, vol. 25, No. 3, pp. 282-289, 2004.

Wilson et al., "Speech Processors for Auditory Prostheses", *Seventh Quarterly Progress Report*, Apr. 1 through Jun. 30, 2000, NIH Project N01-DC-8-2105, pp. 1-38.

Zeng et al., "On the Dichotomy in Auditory Perception Between Temporal Envelope and Fine Structure Cues[a] (L)", *J. Acoust. Soc. Am.*, vol. 116 (3), pp. 1351-1354, Sep. 2004.

Zierhofer, "Analysis of a Linear Model for Electrical Stimulation of Axons—Critical Remarks on the 'Activating Function Concept'", *IEEE Trans. On Biomed Eng*, vol. 48, No. 2, pp. 173-184, Feb. 2001.

Kral et al., "Spacial Resolution of Cochlear Implants: The Electrical Field and Excitation of Auditory Afferents", Hearing Research, 121:11-28, 1998.

Loizou, "Signal Processing for Cochlear Prosthesis: A Tutorial Review," IEEE, vol. 2, pp. 881-885, 1997.

Matsuoka, "Compound Action Potentials Evoked by Electrical Pulse Trains: Effects of Stimulus Parameters on Response Patterns", Thesis at University of Iowa, Jul. 1998.

Wilson et al., "Better Speech Recognition with Cochlear Implants", Nature, 352:236-238, Jul. 1991.

Wilson et al., "Speech Processors for Auditory Prostheses", Seventh Quarterly Progress Report, Feb. 1 through Apr. 30, 1994, NIH Contract N01-DC-2-24-1.

European Patent Office, Partial European Search Report—Application No. 07075655.6-2305—dated Nov. 5, 2008, 7 pages.

International Searching Authority, International Search Report dated Nov. 16, 2005.

International Searching Authority, International Search Report dated Jan. 23, 2007.

International Searching Authority, International Search Report dated Dec. 14, 2000.

Geisler, "From Sound to Synapse", *Oxford University Press, Inc.*, New York, 1998.

Zierhofer et al., "Simultaneous Stimulation Based on Channel Interaction Compensation", 2007 Conference on Implantable Auditory Prostheses, Granlibakken, p. 142, Jul. 2007.

Stickney et al., "Improving Frequency Discrimination in Cochlear Implant Users", The Association for Research in Otolarngology, 30th Annual Midwinter Meeting of the ARO, Denver, Abstract 838, Feb. 2007.

Zierhofer et al., "Simultaneous Intracochlear Stimulation Based on Channel Interaction Compensation: Analysis and First Results", IEEE Transactions on Biomedical Engineering, vol. 55, No. 7, pp. 1907-1916, Jul. 2008.

International Searching Authority, International Search Report—International Application No. PCT/US2008/075984, dated Nov. 26, 2008, together with the Written Opinion of the International Searching Authority, 14 pages.

* cited by examiner

SIMULTANEOUS INTRACOCHLEAR STIMULATION

CROSS REFERENCE TO RELATED APPLICATIONS

This application claims priority from U.S. Provisional Patent Application Ser. No. 60/971,473 filed Sep. 11, 2007, entitled "Simultaneous Intracochlear Stimulation," which is hereby incorporated herein by reference, in its entirety.

This application is also a continuation-in-part of U.S. application Ser. No. 11/685,887 filed Mar. 14, 2007, entitled Electrical Nerve Stimulation Based on Channel Specific Sampling Sequences, now U.S. Pat. No. 7,937,157, which in turn is a continuation of U.S. application Ser. No. 10/303,568 filed Nov. 25, 2002, entitled Electrical Nerve Stimulation Based on Channel Specific Sampling Sequences, which issued as U.S. Pat. No. 7,209,789, which in turn is a continuation of U.S. application Ser. No. 09/648,687 filed Aug. 25, 2000, entitled Electrical Nerve Stimulation Based on Channel Specific Sampling Sequences, which issued as U.S. Pat. No. 6,594,525, and which claims priority from U.S. provisional patent application Ser. No. 60/150,773 filed Aug. 26, 1999, entitled Concept for Electrical Stimulation of the Acoustic Nerve Based on Channel Specific Sampling Sequences (CSSS). Each of the above described applications are hereby incorporated herein by reference.

TECHNICAL FIELD

The present invention relates to electrical nerve stimulation, and more particularly, simultaneous electrical nerve stimulation for cochlear implants

BACKGROUND ART

Cochlear implants and other inner ear prostheses are one option to help profoundly deaf or severely hearing impaired persons. Unlike conventional hearing aids that just apply an amplified and modified sound signal; a cochlear implant is based on direct electrical stimulation of the acoustic nerve. Typically, a cochlear implant stimulates neural structures in the inner ear electrically in such a way that hearing impressions most similar to normal hearing are obtained.

Figure 1:
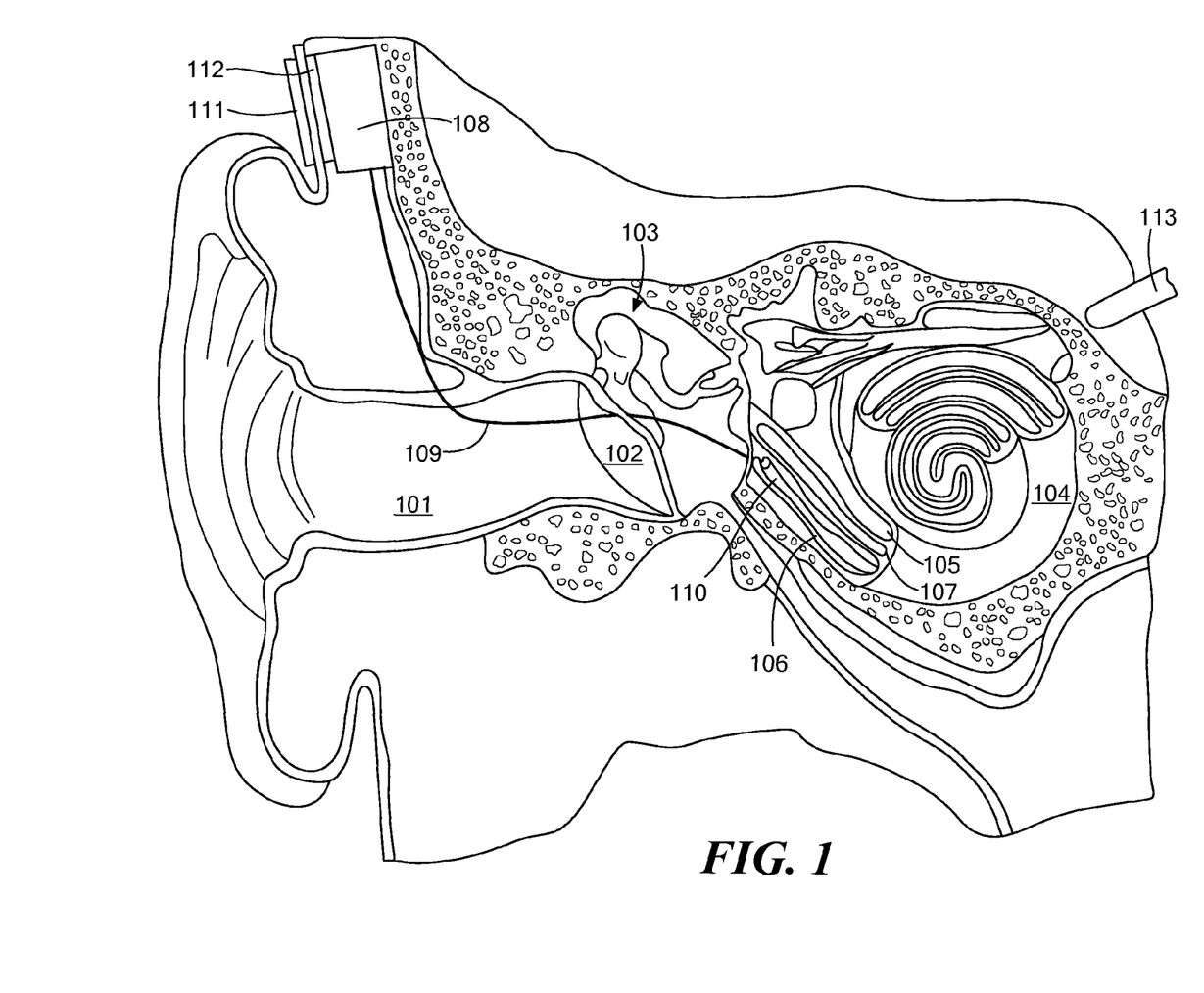
FIG. 1 shows a section view of an ear with a typical cochlear implant system.

FIG. 1 shows a section view of an ear with a typical cochlear implant system. A normal ear transmits sounds through the outer ear 101 to the eardrum 102, which moves the bones of the middle ear 103, which in turn excites the cochlea 104. The cochlea 104 includes an upper channel known as the scala vestibuli 105 and a lower channel known as the scala tympani 106, which are connected by the cochlear duct 107. In response to received sounds transmitted by the middle ear 103, the fluid filled scala vestibuli 105 and scala tympani 106 function as a transducer to transmit waves to generate electric pulses that are transmitted to the cochlear nerve 113, and ultimately to the brain. Frequency processing seems to change in nature from the basal region of the cochlea, where the highest frequency components of a sound are processed, to the apical regions of the cochlea, where the lowest frequencies are analyzed.

Some persons have partial or full loss of normal sensorineural hearing. Cochlear implant systems have been developed to overcome this by directly stimulating the user's cochlea 104. A typical cochlear prosthesis essentially includes two parts: the speech processor and the implanted stimulator 108. The speech processor (not shown in FIG. 1) typically includes a microphone, a power supply (batteries) for the overall system and a processor that is used to perform signal processing of the acoustic signal to extract the stimulation parameters. In state-of-the art prostheses, the speech processor is a behind-the-ear (BTE-) device. The implanted stimulator generates the stimulation patterns and conducts them to the nerve tissue by means of an electrode array 110 which usually is positioned in the scala tympani in the inner ear. The connection between speech processor and stimulator is usually established by means of a radio frequency (RF-) link. Note that via the RF-link both stimulation energy and stimulation information are conveyed. Typically, digital data transfer protocols employing bit rates of some hundreds of kBit/s are used.

One example of a standard stimulation strategy for cochlear implants is called the "Continuous-Interleaved-Sampling (CIS)" strategy, as described by Wilson B S, Finley C C, Lawson D T, Wolford R D, Eddington D K, Rabinowitz W M, "Better speech recognition with cochlear implants," Nature, vol. 352, 236-238, July 1991, which is incorporated herein by reference in its entirety. Signal processing for CIS in the speech processor typically involves the following steps:
1. Splitting up of the audio frequency range into spectral bands by means of a filter bank,
2. Envelope detection of each filter output signal,
3. Instantaneous nonlinear compression of the envelope signal (map law), and.
4. Adaptation to thresholds (THR) and most comfortable loudness (MCL) levels Each of the stimulation electrodes in the scala tympani is typically associated with a band pass filter of the external filter bank. According to the "tonotopic principle" of the cochlea, high frequency bands are associated with electrodes positioned more closely to the base, and low frequency bands to electrodes positioned more deeply in the direction of the apex, as described by Greenwood DD, "A cochlear frequency-position function for several species—29 years later," J. Acoust. Soc. Am., 2593-2604, 1990, which is incorporated herein by reference in its entirety. For stimulation, charge balanced current pulses—usually biphasic symmetrical pulses—are applied. The amplitudes of the stimulation pulses are obtained by sampling the compressed envelope signals. As the characteristic CIS paradigm, For stimulation, symmetrical biphasic current pulses are applied. The amplitudes of the stimulation pulses are directly obtained from the compressed envelope signals (step (3) of above). These signals are sampled sequentially, and the stimulation pulses are applied in a strictly non-overlapping sequence. Thus, as a typical CIS-feature, only one stimulation channel is active at one time. The overall stimulation rate is comparatively high. For example, assuming an overall stimulation rate of 18 kpps, and using an 12 channel filter bank, the stimulation rate per channel is 1.5 kpps. Such a stimulation rate per channel usually is sufficient for adequate temporal representation of the envelope signal.

The influence of various CIS-parameters on speech perception, such as the number of channels and the stimulation rate per channel, etc. has been investigated (see for example: Loizou P C, Poroy O, Dorman M, The effect of parametric variations of cochlear implant processors on speech understanding," J. Acoust. Soc Am. 2000 August; 108(2):790-802; and Wilson B, Wolford R, Lawson D, Speech processors for Auditory prostheses—Seventh quarterly progress report. NIH Project N01-DC-8-2105, each of which is incorporated herein by reference in their entirety) and new concepts aiming at a further improvement have been proposed. For example, one approach is based on the principle of stochastic resonance (see, for example: McNamara B and Wiesenfeld K, "Theory of stochastic resonance" Phys. Rev. A, 39:4854-4869; Rubinstein J T, Wilson B S, Finley C C, Abbas P J, "Pseudospontaneous activity: stochastic independence of auditory nerve fibers with electrical stimulation," Hear. Res. 127, 108-118, 1999; and Morse R P and Evans E F, "Additive noise can enhance temporal coding in a computational model of analogue cochlear implant stimulation," Hear. Res. 133, 107-119, 1999, each of which is incorporated herein by reference in its entirety). The basic idea is to mimic spontaneous activity in the neurons to provide a more natural representation of the envelope signals in the spiking patterns. However, so far this and other approaches have not found their way into broad clinical applications, mainly because no substantial improvement in of CT performance as compared to CIS has been found.

At present, the incorporation of so called "fine structure information" seems to be the most promising way to further improve CIS. Following Hilbert (i.e., Hilbert D, "Grundzüge einer allgemeinen Theorie linearer Integralgleichungen," Teubner, Leipzig, 1912, incorporated herein by reference in its entirety), any signal can be represented as the product of a slowly varying envelope and a rapidly varying signal containing temporal fine structure. The current CIS strategy uses only the envelope information; the fine structure information is discarded. In the response of a CIS band pass filter, temporal fine structure information is represented by position of the zero crossings of the signal and tracks the exact spectral position of the center of gravity of the signal within its band pass region, including temporal transitions of such centers of gravity. For example, the temporal transitions of formant frequencies in vowel spectra are highly important cues for the perception of preceding plosives or other unvoiced utterances. Furthermore, a close look at the details of a band pass filter output reveals that the pitch frequency is clearly present in the temporal structure of the zero crossings. The relative importance of envelope and fine structure information is investigated in an experiment described in Smith Z M, Delgutte B, Oxenham A J, "Chimaeric sounds reveal dichotomies in auditory perception," Nature, vol. 416, 87-90, March 2002, which is incorporated herein by reference in its entirety. There is some consensus that for an intermediate number of 4 to 16 processing channels, the envelope is most important for speech reception whereas the temporal fine structure is most important for pitch perception (melody recognition) and sound localization.

In the light of these results, standard CIS is a good choice with respect to speech intelligibility (e.g., for American English). However, regarding music perception and perception of so called tone languages (e.g., Mandarin Chinese, Cantonese, Vietnamese, That, etc.), CIS might be suboptimal and new stimulation strategies containing both envelope and temporal fine structure information might have the potential for a substantial improvement of CT performance. This assumption is supported, for example, by the study in F G Zeng, K B Nie, S Liu, G S Stickney, E Del Rio, Y Y Kong, H B Chen, "Speech recognition with amplitude and frequency modulations," *Proc. nat. acad. of science* 102: 2293-2298, 2005, which is incorporated by reference in its entirety, where it is demonstrated that slowly varying frequency modulations can be perceived by cochlear implant subjects and thus an appropriate incorporation in future stimulation strategies is recommended.

Considering such new stimulation strategies it is clear that an increase of information will require higher pulse repetition rates per channel. Adhering to the basic CIS-paradigm of strictly non-overlapping pulses, an increase in pulse rates can only be achieved if the pulse durations get shorter. However, the pulse duration cannot be reduced arbitrarily, because shorter pulses require higher pulse amplitudes for sufficient loudness, and pulse amplitudes are limited for various practical reasons, such as a maximum implant supply voltage. Besides, there exists a fundamental neural time constant due to properties of nodes of Ranvier in myelinated nerve fibers, which is about $\tau=20$-$30$ µs in the auditory nerve (see, for example, Frijns J and ten Kate J, "A model of myelinated nerve fibers for electrical prosthesis design," Med. Biol. Eng. Comput., vol 32, pp. 391-398, 1994, which is incorporated herein by reference in its entirety). Although the response of the transmembrane potentials to a stimulation pulse is faster than the response of a simple first order system ("spectral acceleration," see, for example, Zierhofer C M, "Analysis of a linear model for electrical stimulation of axons—critical remarks on the "activating function concept"," IEEE Trans. BME, Vol. 48, No. 2, February 2001, which is incorporated herein by reference in its entirety), phase durations significantly shorter than $\tau$ should be avoided in order to avoid current shortcuts due to the membrane capacitances.

SUMMARY OF THE INVENTION

In accordance with one embodiment of the invention, a method of simultaneously activating at least two electrodes in a multichannel electrode array is presented. The method includes calculating pulse amplitudes of the electrodes in the multichannel array by taking into account parameters of spatial channel interaction reflecting geometric overlapping of electrical fields from each electrode. Calculating is based, at least in part, on place-independent impulse responses characterized by a first exponential decay constant $\alpha$ at a first side of the electrode and a second exponential decay constant $\beta$ at a second side of the electrode, such that the first exponential decay constant $\alpha$ is the same for each electrode in the array, and the second exponential decay constant $\beta$ is the same for each electrode in the array.

In accordance with related embodiments of the invention, calculating may further include applying place-dependent weighting factors to account for place-dependent impulse responses. Calculating may include using properties of a tri-diagonal matrix. The first exponential decay constant $\alpha$ may not equal the second exponential decay constant $\beta$. The method may further include simultaneously activating the at least two electrodes using sign-correlated pulses. Activating the two electrodes may stimulate the acoustic nerve. The multichannel electrode array may use a monopolar configuration having a remote ground. The multichannel electrode array may include a first electrode at the beginning of the array, and a second electrode at the end of the array, and wherein the method for calculating includes introducing a fictitious electrode neighboring at least one of the first electrode and the second electrode.

In further related embodiments of the invention, calculating may include determining a desired potential for a given position relative to the electrode array, the desired potential determined based, at least in part, on a continuous-interleaved-sampling strategy. Amplitudes of the simultaneous, sign-correlated pulses associated with electrodes are calculated by adding resulting potentials from each of the sign-correlated pulses at the given position, so as to provide a total potential at the given position substantially equal to the desired potential.

In accordance with another embodiment of the invention, a cochlear implant system includes a multi-channel electrode array having at least two electrodes. A stimulator calculates amplitudes of electrode stimulation signals associated with the electrodes as a function of spatial channel interaction reflecting geometric overlapping of electrical fields from each electrode. Calculating is based, at least in part, on place-independent impulse responses characterized by a first exponential decay constant α at a first side of the electrode and a second exponential decay constant β at a second side of the electrode, such that the first exponential decay constant α is the same for each electrode in the array, and the second exponential decay constant β is the same for each electrode in the array.

In accordance with related embodiments of the invention, the simulator applies place-dependent weighting factors to account for place-dependent impulse responses when calculating the amplitudes of the electrode stimulation signals. The implant system may use properties of a tri-diagonal matrix to determine the amplitudes of the electrode signals. The first exponential decay constant α may not equal the second exponential decay constant β. The electrode array may be arranged in a monopolar electrode configuration having a remote ground. The stimulator may simultaneously activate the at least two electrodes using sign-correlated pulses. The multi-channel electrode array may be part of a cochlear implant for simulating the acoustic nerve. The system may further include a speech processor that includes a filter bank for receiving an acoustic audio signal, each filter in the bank of filters associated with one of the electrodes in the multi-channel electrode array. The speech processor derives a weighting factor for each electrode in the multi-channel electrode array from an associated channel filter.

In accordance with another embodiment of the invention, a computer program product for use on a computer system for stimulating electrodes in a multichannel electrode array is presented. Each channel is associated with an electrode in the array. The computer program product includes a computer usable medium having computer readable program code thereon. The computer readable program code includes program code for calculating amplitudes of electrode stimulation signals associated with electrodes as a function of spatial channel interaction reflecting geometric overlapping of electrical fields from each electrode. Calculating is based, at least in part, on place-independent impulse responses characterized by a first exponential decay constant α at a first side of the electrode and a second exponential decay constant β at a second side of the electrode, such that the first exponential decay constant α is the same for each electrode in the array, and the second exponential decay constant β is the same for each electrode in the array.

In accordance with related embodiments of the invention, the program code for calculating may further includes program code for applying place-dependent weighting factors to account for place-dependent impulse responses. The program code for calculating may include using properties of a tri-diagonal matrix. The first exponential decay constant α may not equal the second exponential decay constant β. The computer program product may further include program code for simultaneously stimulating the at least two electrodes using sign-correlated pulses. The multichannel electrode array may be part of a cochlear implant for simulating the acoustic nerve. The multichannel electrode array may use a monopolar configuration having a remote ground. The multichannel electrode array may include a first electrode at the beginning of the array, and a second electrode at the end of the array, and wherein the program code for calculating includes introducing a fictitious electrode neighboring at least one of the first electrode and the second electrode.

In further related embodiments of the invention, the program code for calculating may include program code for determining a desired potential for a given position relative to the electrode array, the desired potential determined based, at least in part, on a continuous-interleaved-sampling strategy. Amplitudes of the simultaneous, sign-correlated pulses associated with electrodes are calculated by adding resulting potentials from each of the sign-correlated pulses at the given position, so as to provide a total potential at the given position substantially equal to the desired potential.

BRIEF DESCRIPTION OF THE DRAWINGS

The foregoing features of the invention will be more readily understood by reference to the following detailed description, taken with reference to the accompanying drawings, in which:

FIGS. 3(a-c) shows qualitative pictures of potential distributions in a 12-channel system, where pulses are applied sequentially in electrodes $E_1$, $E_5$, $E_{10}$, $E_{11}$, and $E_{12}$, in accordance with one embodiment of the invention.

DETAILED DESCRIPTION OF SPECIFIC EMBODIMENTS

In illustrative embodiments, a simultaneous stimulation method and system for cochlear implants is presented. A set of sequential stimulation pulses—which would be applied within a time duration of less than or equal to about the absolute refractory period of neurons—is replaced by a set of simultaneous pulses with amplitudes that are adapted taking into account parameters of spatial channel interaction. The computation amount for amplitude adaptation may be reduced significantly, if the unit responses in individual electrodes have exponential decays involving two different decay constants α (towards apex) and β (towards base). As shown in general, in this case the inverse of the channel interaction matrix is tridiagonal. The new paradigm is based on pulses with technically reasonable phase durations. Theoretically the number of pulses per second in an N-channel system may be increased from N to up to $N^2$. Simultaneous stimulation pulses are typically sign-correlated in a monopolar electrode configuration. Results obtained from cochlear implant patients show at least the same speech perception for the standard sequential and the simultaneous paradigm, if both conditions use the same pulse rates.

Simultaneous Stimulation

Sign-Correlated Stimulation Pulses

In various embodiments of the invention, the system uses simultaneous, sign-correlated stimulation pulses in a monopolar electrode configuration. Sign correlated pulses are generally defined by two conditions: (i) All pulses are substantially 100% synchronously in time, and (ii) all pulses have substantially the same current direction (i.e., equal sign).

Figure 2:
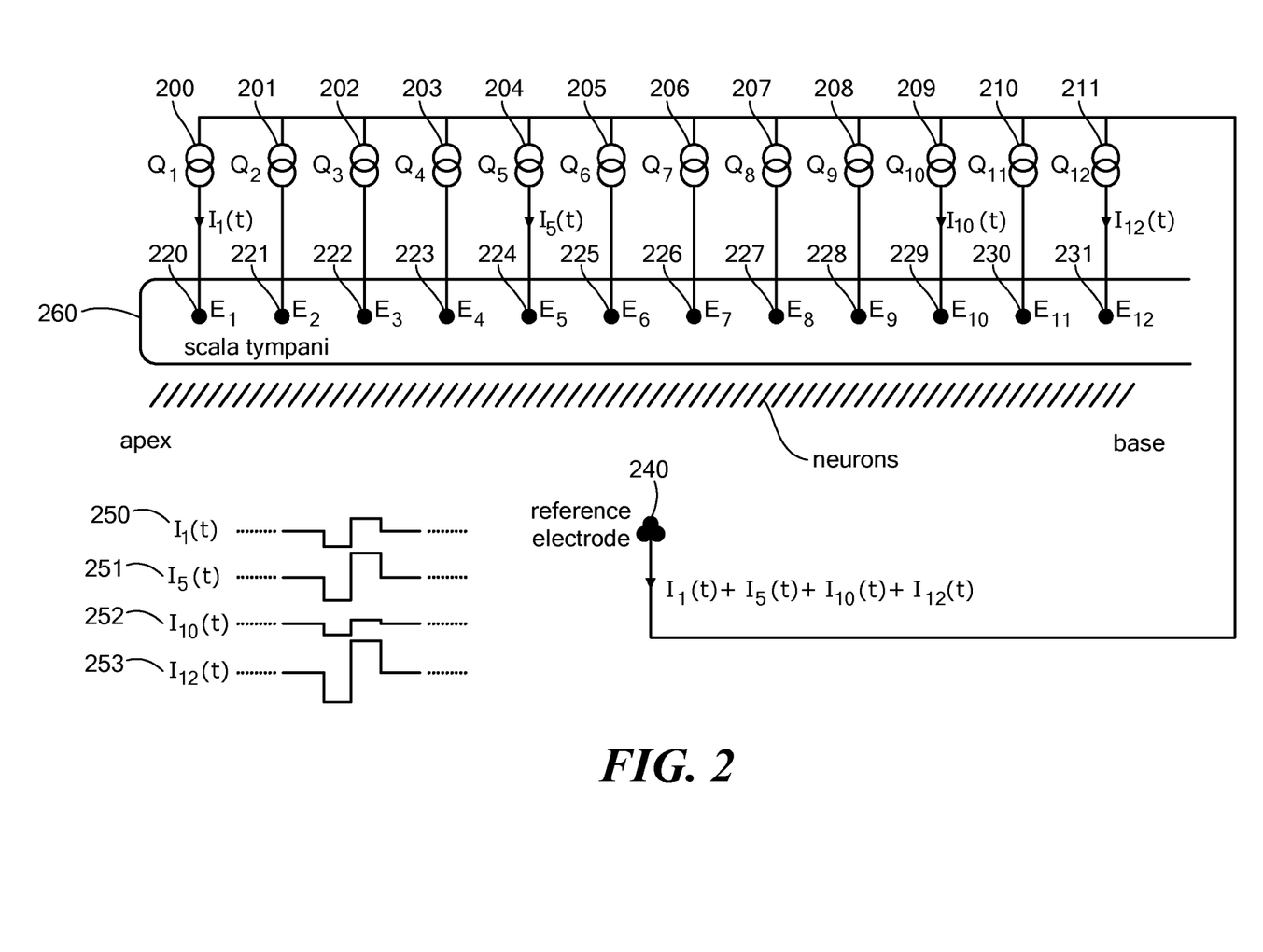
FIG. 2 shows a one-dimensional model of a cochlea and includes a 12-channel electrode array positioned within the scala tympani and a return electrode outside the scala tympani, in accordance with an embodiment of the invention.

FIG. 2 shows a one-dimensional model of a cochlea which is represented by an unrolled conductive tube, and includes a 12-channel electrode array 260 positioned within the scala tympani and a return electrode 240 outside (usually under the temporal muscle), in accordance with one embodiment of the invention. Such a scheme is designated as a monopolar electrode configuration. The electrode array, indicated by electrode contacts $E_1$-$E_{12}$ 220-231, is assumed to be surrounded by fluids and tissues which have a significantly higher electric conductance than the bony cochlear walls (see, for example, Suessermann M F, Spelman F A, "Lumped-parameter model for in vivo cochlear stimulation," IEEE Trans. BME, Vol. 40, No. 3, March 1993, which is incorporated herein by reference in its entirety). The excitable neurons are presumed outside the scala tympani in the so called nerve fiber channel behind the bony spiral lamina (see, for example, Geisler CD "From sound to synapse," ISBN 0-19-510025-5, Oxford University Press, 1998, which is incorporated herein by reference in its entirety). Stimulation pulses are generated in current sources $Q_1$-$Q_{12}$ 200-231. In FIG. 1, sign-correlated biphasic pulses with different amplitudes are generated simultaneously in current sources $Q_1$ 200, $Q_5$ 204, $Q_{10}$ 209, and $Q_{12}$ 211 so as to generate biphasic waveforms $i1(t)$ 250, $i5(t)$ 251, $i10(t)$ 252, and $i12(t)$ 253. The sum of all current pulses is forced to flow through the reference electrode outside the cochlea. However, since all active electrodes are within the same conductive medium, the electrical potentials caused by the individual active electrodes will show considerable geometric overlapping in the scala tympani itself, and at the position of the neurons. This effect is known as spatial channel interaction. However, despite channel interaction, sign correlation in combination with the monopolar configuration ensures that the sum of all currents is flowing into the remote ground electrode 240, i.e., 100% of the charges in both pulse phases are forced to flow through the region of the neurons. Note that this feature is characteristic for the configuration as presented and different to the situation of so called bipolar- or multipolar configurations [see, for example: Van den Honert C, Stypulkowski, "Single fiber mapping of spatial excitation patterns in the electrically stimulated auditory nerve," Hear. Res. 29, 195-206, 1987; and Miyoshi S, Sakajiri M, Ifukube T, Matsushima J, "Evaluation of the tripolar electrode stimulation method by numerical analysis and animal experiments for cochlear implants," Acta Otol. Suppl. 532:123-5, 1997, each of which is incorporated herein by reference). For example, in a bipolar configuration, sink- and source electrodes are both within the scala tympani and separated typically by 1 to 3 mm. The remote ground electrode is omitted. For stimulation, the active electrodes are operated simultaneously with opposite signs of the pulse phases. While this leads to a better concentration of electrical fields in the vicinity of the electrodes and thus defuses channel interaction, there are important disadvantages. Because the high conductance of the intracochlear medium represents a low impedance shunt between the activated electrodes, most of the current is flowing within the scala tympani and does not reach the position of the neurons. As compared to the monopolar configuration, substantially higher stimulation pulse amplitudes are required for suprathreshold stimulation, which results in a significantly increased implant power consumption. In addition, very high current densities occur at metal surfaces of the electrode contacts which might cause safety problems, as described by Brummer S B, Turner M J, "Electrical stimulation with Pt electrodes: II—Estimation of maximum surface redox (theoretical non-gassing) limits," IEEE Trans. BME, Vol. 24, September 1977, which is incorporated by reference in its entirety).

Channel Interaction Compensation—Basic Concept

Figure 3A:
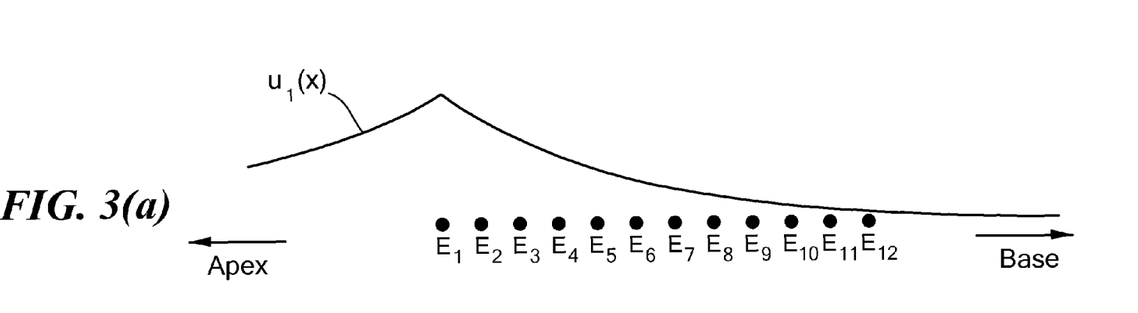
Figure 3B:
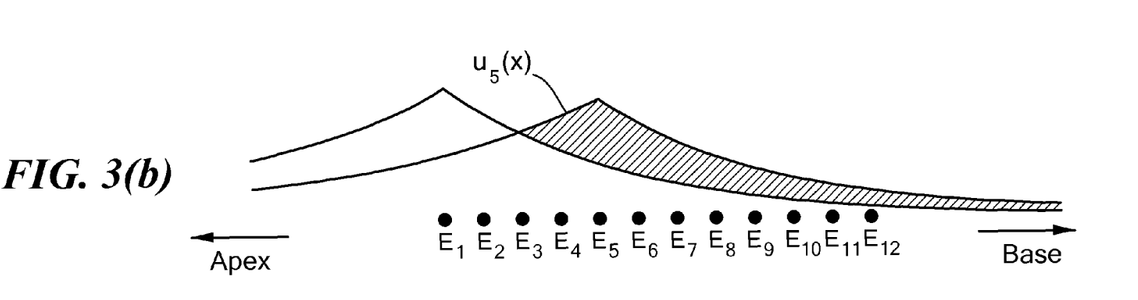
Figure 3C:
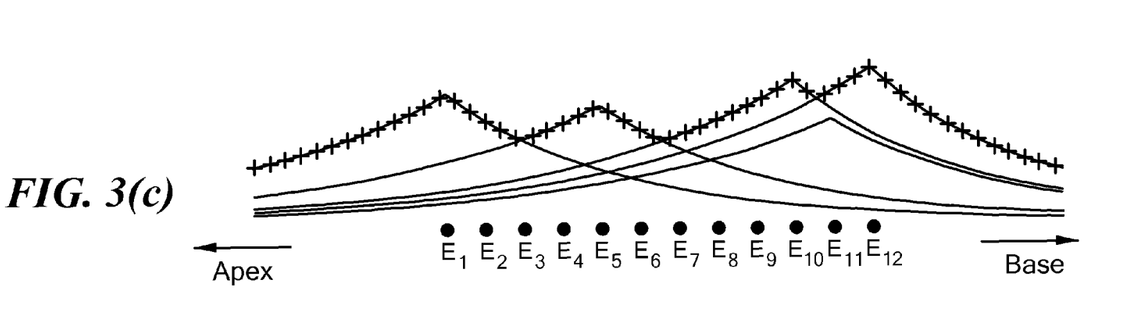

The starting point of the following discussion is a standard CIS paradigm. Consider the voltage potentials in the scala tympani caused by a sequence of sequentially applied biphasic current pulses. In the following only the depolarizing phases of the stimulation pulses are regarded, and for convenience, a positive sign is associated to the respective potential distributions. The simple one-dimensional model of the cochlea as in FIG. 2 is used again, and purely ohmic behavior of the tissue is assumed (see A Kral, R Hartmann, D Mortazavi, R Klinke, "Spatial resolution of cochlear implants: the electrical field and excitation of auditory afferents," Hear. Res. 121, pp. 11-28, July 1998, which is incorporated herein by reference in its entirety). FIGS. 3($a$-$c$) shows qualitative pictures of potential distributions in a 12-channel system, where pulses are applied sequentially in electrodes $E_1$, $E_5$, $E_{10}$, $E_{11}$, and $E_{12}$, in accordance with one embodiment of the invention. A first pulse in E1 occurs as shown in FIG. 3($a$). Regarding the voltage distribution $u_1(x)$ due to the first pulse in electrode $E_1$ (upper panel), most neurons will be activated in the immediate neighborhood of the electrode, and the number of activated neurons will decrease with increasing distance to $E_1$. The second pulse in $E_5$ occurs immediately after the first pulse and causes potential $u_5(x)$, as shown in FIG. 3($b$). However, this pulse will activate less new neurons, because due to spatial channel interaction, $U_5(x)$ is partly masked by $u_1(x)$, and thus many of the neurons in the vicinity of $E_5$ have already been excited by the first pulse. These neurons cannot be retriggered again, because they are in refractory states. As shown in FIG. 3($b$), new neurons may be elicited only according to the hatched area below $u_5(x)$. Similarly, each one of the following pulses can recruit only a fraction of neurons compared to the case where they are activated separately. If all sequential pulses are applied within a period equal to or shorter than about the absolute refractory period of the neurons ($\approx$1 ms), refractory effects in combination with spatial channel interaction will cause a recruitment profile which is roughly derived from the contour potential of the individual sequentially applied potential distributions, as shown in FIG. 3($c$). The pulse in electrode E11 is masked by its predecessors and thus does not contribute to the contour potential Note that in the example in FIGS. 3($a$-$c$), the pulse elicited in electrode $E_{11}$ cannot activate neurons, because the associated potential distribution is fully masked by the potentials of its predecessors.

Figure 4:
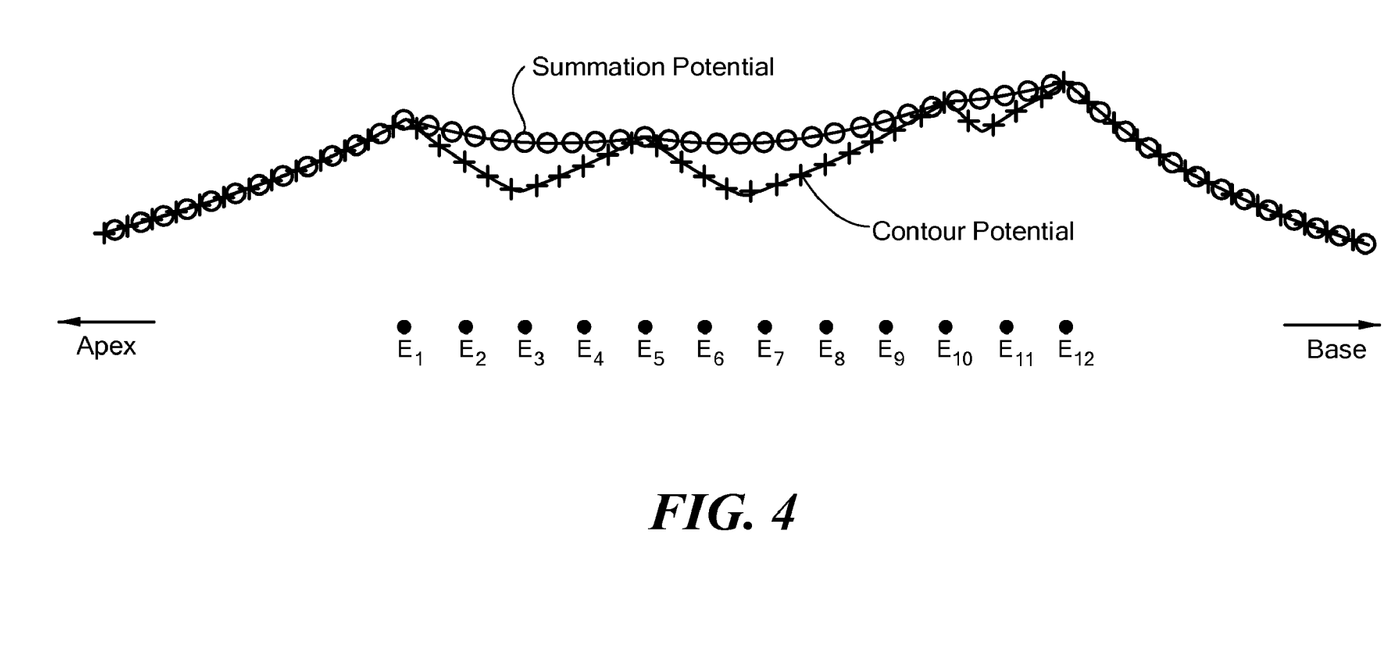
FIG. 4 shows potential distributions of a 12-channel simultaneous stimulation system, in accordance with an embodiment of the invention.

In illustrative embodiments, the contour potential of a set of sequentially applied pulses is approximated by a so called "summation potential", which is generated by a set of sign-correlated simultaneous pulses. The contour potential has to be obtained from sequential pulses which are applied within a time period shorter than about one absolute refractory period of the nerve fibers. It is stipulated that in this case, the summation potential and contour potential essentially cause the same pattern of neuronal activation. The amplitudes of the simultaneous pulses are derived from the sequential amplitudes, but are modified by taking into account spatial potential superposition. Summation- and contour potentials should be equal at the position of the active electrodes. This concept is designated as "channel interaction compensation (CIC)". E.g., if the pulse amplitudes in electrodes $E_1$, $E_5$, $E_{10}$, and $E_{12}$ in the example in FIG. 2 are modified accordingly and applied simultaneously, they result in a summation potential as depicted in FIG. 4. As demanded, summation potential (circles) and contour potentials (+ signs) coincide at the electrode positions. Between these positions, the summation potential is less pronounced as compared to the sequential contour.

Analysis

General Spatial Impulse Responses

Assuming a one-dimensional model of the cochlea and a linear and ohmic behavior of the tissue, the voltage distribution $u_n(x)$ caused by a single current amplitude $I_{sequ,n}$ in electrode number n at position $x_n$ is given by $$u_n(x) = I_{sequ,n} r_n(x - x_n) \quad (1)$$

where function $r_n(x)$ denotes the spatial impulse response associated to electrode number n. Typically, each electrode has its specific response $r_n(x)$, but all responses have in common that the maximum occurs at x=0, and that they are decaying monotonously on both sides (see, for example, Kral A, Hartmann R, Mortazavi D, Klinke R, "Spatial resolution of cochlear implants: the electrical field and excitation of auditory afferents," Hear. Res. 121, 11-28, 1998; and Zierhofer C M, Hochmair-Desoyer I J, Hochmair E S, "Electronic design of a cochlear implant for multichannel high-rate pulsatile stimulation strategies," IEEE Trans. Rehab. Eng., Vol. 3, March 1995, each of which incorporated herein by reference in its entirety).

Thus the peak potentials $U_{max,n}$ at the electrode positions $x = x_n$ are given by $$U_{max,n} = I_{sequ,n} r_n(0) \quad (2)$$

In the current concept it is demanded that simultaneous amplitudes $I_n$ cause a summation potential, which is equal to the peak potentials at the positions of the active electrodes. For convenience, equidistant electrodes with an electrode spacing $d = x_n - x_{n-1}$ are assumed. If all electrodes of an N-channel system are activated simultaneously, the following set of equations is obtained $$U_{max,1} = I_1 r_1(0) + I_2 r_2(-d) + I_3 r_3(-2d) + \ldots + I_N r_N(-(N-1)d)$$

$$U_{max,2} = I_1 r_1(d) + I_2 r_2(0) + I_3 r_3(-d) + \ldots + I_N r_N(-(N-2)d)$$

$$\ldots$$

$$U_{max,N} = I_1 r_1((N-1)d) + I_2 r_2((N-2)d) + I_3 r_3((N-3)d) + \ldots + I_N r_N(0) \quad (3)$$

Using vector notation and inserting (2) in (3) yields the relationship between sequential- and simultaneous amplitudes $$\begin{pmatrix} I_{sequ,1} \\ I_{sequ,2} \\ \ldots \\ I_{sequ,N} \end{pmatrix} = H_0 \begin{pmatrix} I_1 \\ I_2 \\ \ldots \\ I_N \end{pmatrix}, \quad (4)$$

where $H_0$ denotes the so-called "channel interaction matrix"

$$H_0 = \begin{pmatrix} 1 & \frac{r_2(-d)}{r_1(0)} & \ldots & \frac{r_N(-(N-1)d)}{r_1(0)} \\ \frac{r_1(d)}{r_2(0)} & 1 & \ldots & \frac{r_N(-(N-2)d)}{r_2(0)} \\ \ldots & \ldots & \ldots & \ldots \\ \frac{r_1((N-1)d)}{r_N(0)} & \frac{r_2((N-2)d)}{r_N(0)} & \ldots & 1 \end{pmatrix}. \quad (5)$$

The simultaneous amplitudes can be computed with $$\begin{pmatrix} I_1 \\ I_2 \\ \ldots \\ I_N \end{pmatrix} = H_0^{-1} \begin{pmatrix} I_{sequ,1} \\ I_{sequ,2} \\ \ldots \\ I_{sequ,N} \end{pmatrix}, \quad (6)$$

where $H_0^{-1}$ is the inverse of $H_0$. In various CIC applications, not all but only a subset of electrodes will be candidates for simultaneous activation. The system (4) is simplified by removing non-used current amplitudes from the amplitude vectors (both sequential and simultaneous), and delete the corresponding rows and columns from matrix $H_0$. This procedure is designated as "reduction of the CIC system".

In general the simultaneous amplitudes obtained from a CIC procedure can include negative solutions. Negative amplitudes mean that pulses with inverted phases are required to achieve the desired summation potential. However, such pulses contradict the principle of sign-correlation and therefore are not applicable and have to be excluded. This requires another reduction of the CIC system and a re-calculation of the remaining amplitudes with a modified interaction matrix. Theoretically, the new solution can again include negative amplitudes, and thus the procedure of re-calculations is repeated, until a vector with only positive simultaneous amplitudes is obtained. In the most extreme case, only one amplitude remains, and in this case, trivially "simultaneous" and "sequential" amplitudes are equal.

With respect to a practical realization in a cochlear implant system with limited space- and power resources, the iterative CIC-procedure as described is a computational challenge. In particular, matrix inversions cause problems. Standard matrix inversion procedures, such as, e.g., the Gauss-Jordan algorithm, are difficult to implement for real-time operations. On the other hand, storing coefficients of inverted matrices requires lots of memory. A short consideration reveals that for a CIC system with K simultaneous amplitudes, $2^K$ different inverse matrices with an overall number of $$\sum_{i=0}^{K} \binom{K}{i}(K-i)^2$$

matrix coefficients have to be stored. For K=12, this results in 4096 matrices and 159744 coefficients.

Spatial Impulse Responses with Exponential Decays

Place-Independent Impulse Responses

In illustrative embodiments of the invention, the computational cost for CIC may be reduced dramatically, if the impulse responses $r_n(x)$ are assumed to be place-independent functions consisting of two exponentially decaying branches, i.e., $$r_n(x) = r(x) = \begin{cases} r_0 \exp\left(\frac{x}{\lambda_{apex}}\right) & \text{for } x < 0, \text{ and} \\ r_0 \exp\left(-\frac{x}{\lambda_{base}}\right) & \text{for } x \geq 0, \end{cases} \quad (7)$$

with $r_0$ as constant parameter, and $\lambda_{apex}$ and $\lambda_{base}$ as exponential decay constants towards apex and base, respectively. Note that responses (7) represent rather crude approximations to reality. However, as will be demonstrated in subsequent sections, the matrix calculus derived here may be adopted for the more realistic situation of place-dependent impulse responses with exponential decays. Assuming equidistant electrodes with electrode spacing d allows to define two constants $\alpha$ and $\beta$ as $$\alpha = \exp\left(-\frac{d}{\lambda_{apex}}\right), \text{ and} \quad (8)$$

$$\beta = \exp\left(-\frac{d}{\lambda_{base}}\right).$$

With $\alpha$ and $\beta$, inserting (7) into (5) yields an interaction matrix $$H = \begin{pmatrix} 1 & \alpha & \alpha^2 & \dots & \alpha^{N-1} \\ \beta & 1 & \alpha & \dots & \alpha^{N-2} \\ \beta^2 & \beta & 1 & \dots & \alpha^{N-3} \\ \dots & \dots & \dots & \dots & \dots \\ \beta^{N-1} & \beta^{N-2} & \beta^{N-3} & \dots & 1 \end{pmatrix}. \quad (9)$$

Fortunately, this matrix H has remarkably advantageous properties, as will be shown in the following. As a first important feature, matrix H is non-singular, if the decay constants are within the ranges [0≦α<1] and [0≦β<1]. This can easily be seen, because individual lines and rows are certainly not linear dependent from each other. With (9), system (4) can be written as $$I_{sequ,1} = I_1 + \alpha I_2 + \alpha^2 I_3 + \alpha^3 I_4 + \dots + \alpha^{N-1} I_N$$

$$I_{sequ,2} = \beta I_1 + I_2 + \alpha I_3 + \alpha^2 I_4 + \dots + \alpha^{N-2} I_N$$

$$I_{sequ,3} = \beta^2 I_1 + \beta I_2 + I_3 + \alpha I_4 + \dots + \alpha^{N-3} I_N$$

$$\dots$$

$$I_{sequ,N} = \beta^{N-1} I_1 + \beta^{N-2} I_2 + \beta^{N-3} I_3 + \beta^{N-4} I_4 + \dots + I_N. \quad (10)$$

For the following discussion—consistent with FIG. 3—electrode indices are assumed to increase from apex to base, i.e., from left to right. In a CIC reduction procedure typically a subset of electrodes is selected, and equations for unused sequential amplitudes are deleted and unused simultaneous amplitudes are set to zero. For example, consider a 12-channel system, where the electrodes with indices 3, 5, 8, 9, and 11 have been selected for simultaneous stimulation. Electrode 3 is the leftmost electrode with its next neighbor 5 to the right, and electrode 11 is the rightmost electrode with its next neighbor 9 to the left. Electrodes 5, 8, and 9 have two neighbors, i.e., 3 and 8, 5 and 9, and 8 and 11, respectively. In general, if an electrode with index k has two neighbors with indices $k-L_1$ and $k+L_2$ ($L_1 \geq 1, L_2 \geq 1$), the associated amplitudes are $I_{sequ,k}$, $I_{sequ,k-L_1}$ and $I_{sequ,k+L_2}$. The definition of polynomials $\sigma_n$ and $\rho_n$ (n=1, 2, ..., N)

$$\sigma_n = \sum_{i=1}^{n} \beta^{n-i} I_i = \beta^{n-1} I_1 + \beta^{n-2} I_2 + \dots + I_n \quad (11)$$

$$\rho_n = \sum_{i=n}^{N} \alpha^{i-n} I_i = I_n + \alpha I_{n+1} + \dots + \alpha^{N-n} I_N$$

allows to express amplitude $I_{sequ,k}$ and the two neighboring amplitudes $I_{sequ,k-L_1}$ and $I_{sequ,k+L_2}$ as $$I_{sequ,k-L_1} = \sigma_{k-L_1} + \rho_{k-L_1} - I_{k-L_1}$$

$$I_{sequ,k} = \sigma_k + \rho_k - I_k$$

$$I_{sequ,k+L_2} = \sigma_{k+L_2} + \rho_{k+L_2} - I_{k+L_2}. \quad (12)$$

A detailed look at (10) reveals the following identities $$\sigma_{k-L_1} = \frac{1}{\beta^{L_1}}(\sigma_k - I_k) \quad (13)$$

$$\rho_{k-L_1} - I_{k-L_1} = \alpha^{L_1} \rho_k,$$

and $$\rho_{k+L_2} = \frac{1}{\alpha^{L_2}}(\rho_k - I_k) \quad (14)$$

$$\sigma_{k+L_2} - I_{k+L_2} = \beta^{L_2} \sigma_k.$$

Inserting (13) and (14) into (12) yields $$I_{sequ,k-L_1} = \frac{1}{\beta^{L_1}} \sigma_k + \alpha^{L_1} \rho_k - \frac{1}{\beta^{L_1}} I_k \quad (15)$$

$$I_{sequ,k} = \sigma_k + \rho_k - I_k$$

$$I_{sequ,k+L_2} = \beta^{L_2} \sigma_k + \frac{1}{\alpha^{L_2}} \rho_k - \frac{1}{\alpha^{L_2}} I_k.$$

This system is composed of three equations with three unknown variables $\sigma_k$, $\rho_k$, and $I_k$. Isolation of $I_k$ results in $$I_k = a(L_1) I_{sequ,k-L_1} + b(L_1, L_2) I_{sequ,k} + c(L_2) I_{sequ,k+L_2}, \quad (16)$$

with $$a(L_1) = \frac{-\beta^{L_1}}{1 - (\alpha\beta)^{L_1}} \quad (17)$$

$$b(L_1, L_2) = \frac{1 - (\alpha\beta)^{L_1+L_2}}{(1 - (\alpha\beta)^{L_1})(1 - (\alpha\beta)^{L_2})}$$

$$c(L_2) = \frac{-\alpha^{L_2}}{1 - (\alpha\beta)^{L_2}}.$$

Thus, in general, a simultaneous amplitude $I_k$ may be fully determined by the sequential amplitude $I_{sequ,k}$ in the same electrode, and the two sequential amplitudes $I_{sequ,k-L_1}$ and $I_{sequ,k+L_2}$ in the neighboring active electrodes. The weighting factors $a(L_1)$, $b(L_1, L_2)$, and $c(L_2)$ depend on the distances $L_1$ to the lower, and $L_2$ to the upper active neighbors.

The leftmost and rightmost active electrodes may need special consideration. The leftmost active electrode has no neighbor at positions with lower indices. However, the summation potential in the direction of lower electrode addresses is decreasing exponentially according to decay parameter $\alpha$. Thus, if $I_{sequ,k}$ represents the amplitude of the leftmost amplitude, a (fictitious) neighboring electrode at position k−1 ($L_1$=1) with an amplitude $\alpha I_{sequ,k}$ may be introduced. Inserting into (16) yields $$I_k = a(1)\alpha I_{sequ,k} + b(1, L_2) I_{sequ,k} + c(L_2) I_{sequ,k+L_2} = \quad (18)$$

$$= (\alpha a(1) + b(1, L_2)) I_{sequ,k} + c(L_2) I_{sequ,k+L_2} =$$

$$= b_0(L_2) I_{sequ,k} + c(L_2) I_{sequ,k+L_2}.$$

With (17), coefficient $b_0(L_2)$ becomes $$b_0(L_2) = \alpha a(1) + b(1, L_2) = \frac{1}{1-(\alpha\beta)^{L2}}. \quad (19)$$

Similarly, the rightmost active electrode has no neighbor at higher electrode positions. In this region, the summation potential is exponentially decaying according to β. If $I_{sequ,k}$ represents the amplitude of the rightmost amplitude, a (fictitious) neighboring electrode at position k+1 ($L_2$=1) with resulting amplitude $\beta I_{sequ,k}$ can be may be introduced. Inserting into (16) yields $$I_n = a(L_1)I_{sequ,k-L1} + b(L_1, 1)I_{sequ,k} + c(1)\beta I_{sequ,k} = \quad (20)$$

$$= a(L_1)I_{sequ,k-L1} + (b(L_1, 1) + \beta c(1))I_{sequ,k} =$$

$$= a(L_1)I_{sequ,k-L1} + b_0(L_1)I_{sequ,k}.$$

With (17), coefficient $b_0(L_1)$ becomes $$b_0(L_1) = b(L_1, 1) + \beta c(1) = \frac{1}{1-(\alpha\beta)^{L1}}. \quad (21)$$

With (17), (19), and (21) the inverse matrix $H^{-1}$ of (9) is given by $$H^{-1} = \begin{pmatrix} b_0(1) & c(1) & 0 & \ldots & 0 & 0 & 0 \\ a(1) & b(1,1) & c(1) & \ldots & 0 & 0 & 0 \\ 0 & a(1) & b(1,1) & \ldots & 0 & 0 & 0 \\ \ldots & \ldots & \ldots & \ldots & \ldots & \ldots & \ldots \\ 0 & 0 & 0 & \ldots & b(1,1) & c(1) & 0 \\ 0 & 0 & 0 & \ldots & a(1) & b(1,1) & c(1) \\ 0 & 0 & 0 & \ldots & 0 & a(1) & b_0(1) \end{pmatrix}. \quad (22)$$

Matrix $H^{-1}$ is tri-diagonal with non-zero coefficients only in the three main diagonals. In case of a system reduction, rows and columns of H are deleted resulting in a reduced matrix H'. As derived earlier, the resulting inverse $H'^{-1}$ is tri-diagonal again, and beside the difference in matrix sizes, only "local changes" of coefficients occur. Thus, if a vector of simultaneous amplitudes has been computed and if it contains negative solutions, these negative solutions need to be removed. Only amplitudes which have been neighboring to the negative amplitudes have to be re-calculated. This feature is extremely advantageous in an iterative CIC procedure.

For example, consider a 12-channel system with simultaneous stimulation of electrodes $E_1$, $E_5$, $E_{10}$, $E_{11}$, and $E_{12}$. The resulting reduced system is given by $$\begin{pmatrix} I_1 \\ I_5 \\ I_{10} \\ I_{11} \\ I_{12} \end{pmatrix} = H'^{-1} \begin{pmatrix} I_{sequ,1} \\ I_{sequ,5} \\ I_{sequ,10} \\ I_{sequ,11} \\ I_{sequ,12} \end{pmatrix} = \quad (23)$$

$$= \begin{pmatrix} b_0(4) & c(4) & 0 & 0 & 0 \\ a(4) & b(4,5) & c(5) & 0 & 0 \\ 0 & a(5) & b(5,1) & c(1) & 0 \\ 0 & 0 & a(1) & b(1,1) & c(1) \\ 0 & 0 & 0 & a(1) & b_0(1) \end{pmatrix} \begin{pmatrix} I_{sequ,1} \\ I_{sequ,5} \\ I_{sequ,10} \\ I_{sequ,11} \\ I_{sequ,12} \end{pmatrix}$$

The distances between active electrodes are directly reflected in the matrix coefficients of $H'^{-1}$. Assuming that the computation of the simultaneous amplitudes yields a negative result $I_{11}$, a further system reduction is required. Amplitudes $I_{sequ,11}$ and $I_{11}$ are removed from the amplitude vectors, and the fourth row and column from $H'^{-1}$. The resulting new system is $$\begin{pmatrix} I_1 \\ I_5 \\ I_{10} \\ I_{12} \end{pmatrix} = H''^{-1} \begin{pmatrix} I_{sequ,1} \\ I_{sequ,5} \\ I_{sequ,10} \\ I_{sequ,12} \end{pmatrix} = \quad (24)$$

$$= \begin{pmatrix} b_0(4) & c(4) & 0 & 0 \\ a(4) & b(4,5) & c(5) & 0 \\ 0 & a(5) & b(5,2) & c(2) \\ 0 & 0 & a(2) & b_0(2) \end{pmatrix} \begin{pmatrix} I_{sequ,1} \\ I_{sequ,5} \\ I_{sequ,10} \\ I_{sequ,12} \end{pmatrix}.$$

Note that the coefficients in rows 1 and 2 of matrices $H'^{-1}$ and $H''^{-1}$ have not changed, and thus the amplitudes $I_1$ and $I_5$ do not have to be re-calculated. Coefficient changes affect only rows (and columns) 3 and 4 of $H''^{-1}$, and thus only electrodes 10 and 12, the previous neighbors of electrode 11, change their amplitude due to new mutual distances.

The amount of memory required to store coefficients $a(L_1)$, $b(L_1, L_2)$, $c(L_2)$, $b_0(L_2)$, $b_0(L_1)$ of all possible inverse matrices of an K-channel CIC system is very low as compared to a CIC system with arbitrary responses. Using $b(L_1, L_2)=b(L_2, L_1)$, a short calculation shows that an overall number of possible coefficients is $$\frac{1}{4}K(K+2) + 2K - 3$$

for even K, and $$\frac{1}{4}(K+1)^2 + 2K - 3$$

for odd K. For K=12, this yields 63 coefficients, which is substantially less than the 159744 coefficients of the general system.

Place-Dependent Impulse Responses

In general, the spatial impulse responses depend on the electrode position. Several reasons contribute to this, i.e., the varying diameter of the scala tympani, and also the varying diameter of the intracochlear electrode array. For example, impulse responses measured show approximately exponential decays in all electrodes, whereby the slopes towards the apex are shallower than towards the base (i.e., α>β), and the maxima in general are higher in the apical, than in the basal region (see A Kral, R Hartmann, D Mortazavi, R Klinke, "Spatial resolution of cochlear implants: the electrical field and excitation of auditory afferents," *Hear. Res.* 121, pp. 11-28, July 1998, which is incorporated by reference it its entirety). Impulse responses like this can be approximated by multiplying r(x) in (7) with electrode specific weighting factors $c_n$ (n=1, 2, ..., N), i.e., $$r_n(x) = \begin{cases} c_n r_0 \exp\left(\dfrac{x}{\lambda_{apex}}\right) & \text{for } x < 0, \text{ and} \\ c_n r_0 \exp\left(-\dfrac{x}{\lambda_{base}}\right) & \text{for } x \geq 0. \end{cases} \quad (25)$$

Inserting (25) into (5), and with definitions (8) for $\alpha$ and $\beta$, the resulting interaction matrix is $$H_c = \begin{pmatrix} 1 & \dfrac{c_2}{c_1}\alpha & \dfrac{c_3}{c_1}\alpha^2 & \cdots & \dfrac{c_N}{c_1}\alpha^{N-1} \\ \dfrac{c_1}{c_2}\beta & 1 & \dfrac{c_3}{c_2}\alpha & \cdots & \dfrac{c_N}{c_1}\alpha^{N-2} \\ \dfrac{c_1}{c_3}\beta^2 & \dfrac{c_2}{c_3}\beta & 1 & \cdots & \dfrac{c_N}{c_1}\alpha^{N-3} \\ \cdots & \cdots & \cdots & \cdots & \cdots \\ \dfrac{c_1}{c_N}\beta^{N-1} & \dfrac{c_2}{c_N}\beta^{N-2} & \dfrac{c_3}{c_N}\beta^{N-3} & \cdots & 1 \end{pmatrix}. \quad (26)$$

It can easily be shown that $H_c$ may be represented as a matrix product $$H_c = C^{-1} H C, \quad (27)$$

where C is a diagonal matrix containing factors $c_n$, i.e., $$C = \begin{pmatrix} c_1 & 0 & 0 & \cdots & 0 \\ 0 & c_2 & 0 & \cdots & 0 \\ 0 & 0 & c_3 & \cdots & 0 \\ \cdots & \cdots & \cdots & \cdots & \cdots \\ 0 & 0 & 0 & \cdots & c_N \end{pmatrix}. \quad (28)$$

With (27) the inverse interaction matrix is simply $$H_c^{-1} = C^{-1} H^{-1} C. \quad (29)$$

Inserting $H_c^{-1}$ into (5) yields $$\begin{pmatrix} I_1 \\ I_2 \\ I_3 \\ \cdots \\ I_N \end{pmatrix} = C^{-1} H^{-1} C \begin{pmatrix} I_{sequ,1} \\ I_{sequ,2} \\ I_{sequ,3} \\ \cdots \\ I_{sequ,N} \end{pmatrix}, \quad (30)$$

which can be expressed as $$\begin{pmatrix} c_1 I_1 \\ c_2 I_2 \\ c_3 I_3 \\ \cdots \\ c_N I_N \end{pmatrix} = H^{-1} \begin{pmatrix} c_1 I_{sequ,1} \\ c_2 I_{sequ,2} \\ c_3 I_{sequ,3} \\ \cdots \\ c_N I_{sequ,N} \end{pmatrix}. \quad (31)$$

This represents a system based on matrix H as used for place independent responses. Place dependence is incorporated by multiplying the sequential amplitudes with their associated weights, and dividing the CIC results by their respective weights. Regarding a practical realization of a CIC system, the computational amount is only slightly increased as compared to place independent responses r(x). However, all computational advantages of matrix H concerning iterative CIC procedures and matrix inversions can still be fully exploited.

Place-Dependent Impulse Responses with Exponentially Distributed Weights

Figure 5:
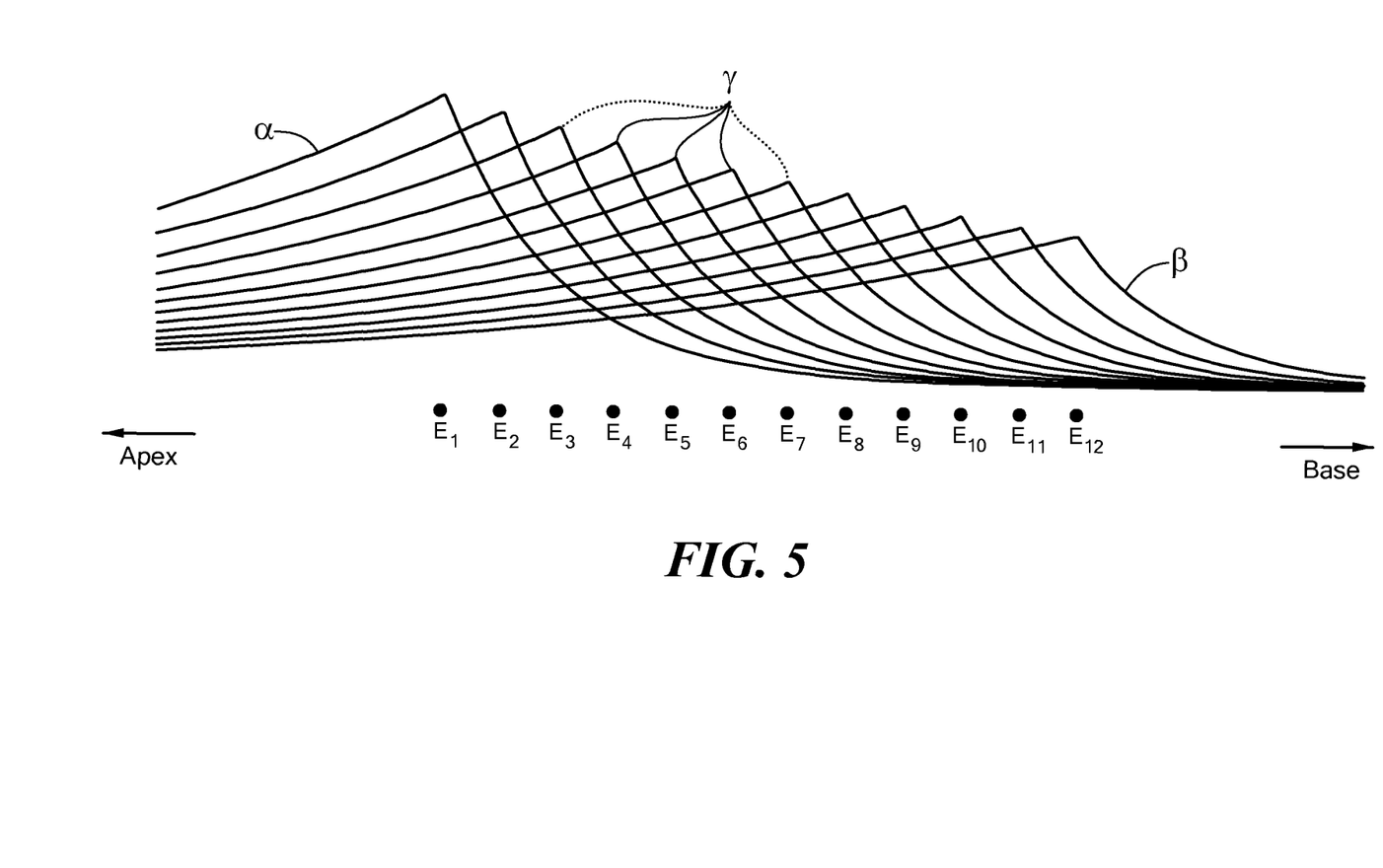
FIG. 5 shows place dependent impulse responses, in accordance with an embodiment of the invention.

A mathematically elegant solution may be obtained for the special case, when the weights $c_n$ in (25) are assumed to be distributed exponentially, i.e., $c_n = \gamma^n$ (n=1, 2, ..., N), with $\gamma$ as a constant. For example, FIG. 5 shows place dependent impulse responses, in accordance with one embodiment of the invention. Each impulse response has a decay constant $\alpha$ (towards apex) and $\beta$ (towards base). A place dependent weighting factor is located on an exponential curve defined by parameter $\gamma$.

The impulse responses $r_n(x)$ are $$r_n(x) = \begin{cases} \gamma^n r_0 \exp\left(\dfrac{x}{\lambda_{apex}}\right) & \text{for } x < 0, \text{ and} \\ \gamma^n r_0 \exp\left(-\dfrac{x}{\lambda_{base}}\right) & \text{for } x \geq 0, \end{cases} \quad (32)$$

and matrix $H_c$ in (26) can directly be expressed as $$H_c = \begin{pmatrix} 1 & \gamma\alpha & (\gamma\alpha)^2 & \cdots & (\gamma\alpha)^{N-1} \\ \dfrac{\beta}{\gamma} & 1 & \gamma\alpha & \cdots & (\gamma\alpha)^{N-2} \\ \left(\dfrac{\beta}{\gamma}\right)^2 & \dfrac{\beta}{\gamma} & 1 & \cdots & (\gamma\alpha)^{N-3} \\ \cdots & \cdots & \cdots & \cdots & \cdots \\ \left(\dfrac{\beta}{\gamma}\right)^{N-1} & \left(\dfrac{\beta}{\gamma}\right)^{N-2} & \left(\dfrac{\beta}{\gamma}\right)^{N-3} & \cdots & 1 \end{pmatrix} \quad (33)$$

This matrix $H_c$ is identical to a matrix H in (9), when constants $\alpha$ and $\beta$ simply are replaced by $\alpha'$ and $\beta'$ with $$\alpha' = \gamma\alpha, \text{ and} \quad (34)$$

$$\beta' = \dfrac{\beta}{\gamma}.$$

Thus, in various embodiments of the invention, each CIC system described by parameters $\alpha$, $\beta$, and $\gamma$ may be transformed into an equivalent CIC system with parameters $\alpha'$ and $\beta'$, and all computational benefits of CIC, based on place-independent impulse responses, can be exploited. Note that the ($\alpha$, $\beta$, $\gamma$) and ($\alpha'$, $\beta'$) systems represent different systems, whose (continuous) summation potentials coincide at the positions of the active electrodes, but are different at all other places.

SUMMARY AND CONCLUSION

The stimulation concept presented above is based on sign-correlated simultaneous pulses. Compared to sequential pulsatile stimulation, simultaneous amplitudes are modified by taking into account parameters of intracochlear potential spread. The simultaneous approach presented here may be the basis for future stimulation strategies, because it allows for a very substantial increase of the overall stimulation rates without the need to reduce pulse phases to unphysiologically low durations. In particular, a better representation of temporal fine structure information should be possible. As an upper theoretical limit, for a N-channel sequential system, the pulse rate can be increased by a factor of N.

An efficient implementation of the CIC algorithm is possible, if for each stimulation electrode the spatial impulse response can be approximated by two exponentially decaying branches with decay constants $\alpha$ towards the apex, and $\beta$ towards the base. This is also valid for the case when the impulse responses are place-dependent and differ by a constant factor. In particular, the properties of a tri-diagonal inverse interaction matrix can be exploited.

If the simultaneous stimulation paradigm is not used to increase the overall stimulation rate, but the overall stimulation rate is kept constant instead, simultaneous pulses with longer phase durations and reduced pulse amplitudes may be utilized. This advantageously results in a substantial reduction of the power consumption.

Alternative embodiments of the invention, may be implemented as, or otherwise include, a computer program product for use with a computer system. Such implementation may include a series of computer instructions fixed either on a tangible medium, such as a computer readable media (e.g., a diskette, CD-ROM, ROM, or fixed disk), or fixed in a computer data signal embodied in a carrier wave that is transmittable to a computer system via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web).

The described embodiments of the invention are intended to be merely exemplary and numerous variations and modifications will be apparent to those skilled in the art. All such variations and modifications are intended to be within the scope of the present invention as defined in the appended claims.

What is claimed is:

1. A method of simultaneously activating at least two electrodes in a multichannel electrode array, the method comprising:
    calculating pulse amplitudes of the electrodes in the multichannel array by taking into account parameters of spatial channel interaction reflecting geometric overlapping of electrical fields from each electrode, wherein calculating is based, at least in part, on place-independent impulse responses characterized by a first exponential decay constant $\alpha$ at a first side of the electrode and a second exponential decay constant $\beta$ at a second side of the electrode, such that the first exponential decay constant $\alpha$ is the same for each electrode in the array, and the second exponential decay constant $\beta$ is the same for each electrode in the array.

2. The method according to claim 1, wherein calculating further includes applying place-dependent weighting factors to account for place-dependent impulse responses.

3. The method of claim 1, wherein calculating includes using properties of a tri-diagonal matrix.

4. The method according to claim 1, wherein the first exponential decay constant $\alpha$ does not equal the second exponential decay constant $\beta$.

5. The method of claim 1, wherein calculating includes;
    determining a desired potential for a given position relative to the electrode array, the desired potential determined based, at least in part, on a continuous-interleaved-sampling strategy;
    determining amplitudes of simultaneous, sign-correlated pulses associated with the electrodes by adding resulting potentials from each of the sign-correlated pulses at the given position, so as to provide a total potential at the given position substantially equal to the desired potential.

6. The method according to claim 1, further comprising simultaneously activating the at least two electrodes using sign-correlated pulses so as to stimulate the acoustic nerve.

7. The method according to claim 1, wherein the multichannel electrode array uses a monopolar configuration having a remote ground.

8. The method according to claim 1, wherein the multichannel electrode array includes a first electrode at the beginning of the array, and a second electrode at the end of the array, and wherein the method for calculating includes introducing a fictitious electrode neighboring at least one of the first electrode and the second electrode.

9. A cochlear implant system comprising:
    a multi-channel electrode array including at least two electrodes; and
    a stimulator that calculates amplitudes of electrode stimulation signals associated with the electrodes as a function of spatial channel interaction reflecting geometric overlapping of electrical fields from each electrode, wherein calculating is based, at least in part, on place-independent impulse responses characterized by a first exponential decay constant $\alpha$ at a first side of the electrode and a second exponential decay constant $\beta$ at a second side of the electrode, such that the first exponential decay constant $\alpha$ is the same for each electrode in the array, and the second exponential decay constant $\beta$ is the same for each electrode in the array.

10. The system according to claim 9, wherein the simulator applies place-dependent weighting factors to account for place-dependent impulse responses when calculating the amplitudes of the electrode stimulation signals.

11. The implant system according to claim 9, wherein the first exponential decay constant $\alpha$ does not equal the second exponential decay constant $\beta$.

12. The implant system according to claim 9, wherein the stimulator uses properties of a tri-diagonal matrix to determine the amplitudes of the electrode signals.

13. The implant system according to claim 9, wherein the electrode array is arranged in a monopolar electrode configuration having a remote ground.

14. The implant system according to claim 9, wherein the stimulator simultaneously activates the at least two electrodes using sign-correlated pulses.

15. The implant system according to claim 9, further comprising a speech processor that includes a filter bank for receiving an acoustic audio signal, each filter in the bank of filters associated with one of the electrodes in the multi-channel electrode array, and wherein the speech processor derives a weighting factor for each electrode in the multi-channel electrode array from an associated channel filter.

16. The implant system according to claim 9, wherein the multichannel electrode array includes a first electrode at the beginning of the array, and a second electrode at the end of the array, and wherein the stimulator introduces a fictitious electrode neighboring at least one of the first electrode and the second electrode when calculating the amplitudes.

17. A non-transitory computer program product for use on a computer system for stimulating electrodes in a multichannel electrode array, each channel associated with an electrode in the array, the computer program product comprising a computer usable medium having computer readable program code thereon, the computer readable program code including:

program code for calculating amplitudes of electrode stimulation signals associated with the electrodes in the electrode array as a function of spatial channel interaction reflecting geometric overlapping of electrical fields from each electrode, wherein calculating is based, at least in part, on place-independent impulse responses characterized by a first exponential decay constant $\alpha$ at a first side of the electrode and a second exponential decay constant $\beta$ at a second side of the electrode, such that the first exponential decay constant $\alpha$ is the same for each electrode in the array, and the second exponential decay constant $\beta$ is the same for each electrode in the array.

18. The non-transitory computer program product according to claim 17, wherein the program code for calculating further includes program code for applying place-dependent weighting factors to account for place-dependent impulse responses.

19. The non-transitory computer program product according to claim 17, wherein the program code for calculating includes program code for using properties of a tri-diagonal matrix.

20. The non-transitory computer program product according to claim 17, wherein the first exponential decay constant $\alpha$ does not equal the second exponential decay constant $\beta$.

21. The non-transitory computer program product according to claim 17, wherein the program code for calculating includes;

program code for determining a desired potential for a given position relative to the electrode array, the desired potential determined based, at least in part, on a continuous-interleaved-sampling strategy;

program code for determining amplitudes of simultaneous, sign-correlated pulses associated with at least two electrodes of the multi-channel array by adding resulting potentials from each of the sign-correlated pulses at the given position, so as to provide a total potential at the given position substantially equal to the desired potential.

22. The non-transitory computer program product according to claim 17, further comprising program code for simultaneously stimulating the at least two electrodes using sign-correlated pulses.

23. The non-transitory computer program product according to claim 17, wherein the multichannel electrode array includes a first electrode at the beginning of the array, and a second electrode at the end of the array, and wherein the program code for calculating includes program code for introducing a fictitious electrode neighboring at least one of the first electrode and the second electrode.

* * * * *

UNITED STATES PATENT AND TRADEMARK OFFICE
CERTIFICATE OF CORRECTION

| | | |
|---|---|---|
| PATENT NO. | : 8,165,686 B2 | Page 1 of 1 |
| APPLICATION NO. | : 12/208793 | |
| DATED | : April 24, 2012 | |
| INVENTOR(S) | : Clemens M. Zierhofer | |

It is certified that error appears in the above-identified patent and that said Letters Patent is hereby corrected as shown below:

In Col. 18, line 54
replace "simulator"
with --stimulator--

Signed and Sealed this
Tenth Day of July, 2012

David J. Kappos
*Director of the United States Patent and Trademark Office*